United States Patent [19]

Iwata et al.

[11] Patent Number: 4,830,497
[45] Date of Patent: May 16, 1989

[54] PATTERN INSPECTION SYSTEM

[75] Inventors: Satoshi Iwata; Moritoshi Ando, both of Atsugi, Japan

[73] Assignee: Fujitsu Limited, Kawasaki, Japan

[21] Appl. No.: 47,480

[22] Filed: May 11, 1987

[30] Foreign Application Priority Data

May 10, 1986 [JP] Japan .................................. 61-107407
Jun. 20, 1986 [JP] Japan .................................. 61-142940

[51] Int. Cl.$^4$ .............................................. G01K 9/00
[52] U.S. Cl. ......................................... 356/394; 382/8
[58] Field of Search ..................... 356/394, 398; 382/8

[56] References Cited

U.S. PATENT DOCUMENTS 4,500,202 2/1985 Smyth ................................. 356/394

Primary Examiner—Richard A. Rosenberger
Attorney, Agent, or Firm—Staas & Halsey

[57] ABSTRACT

An improved pattern inspection system for automatically inspecting patterns on a printed circuit board, a semiconductor chip, etc. The pattern inspection system includes an optical sensor, a binary conversion circuit, a memory storing binary converted data in a matrix form, a length measurement circuit, a reference circuit and a determination circuit. The length measurement circuit includes a gate unit for picking-up the binary converted data array from the memory in radial directions with respect to an origin and for a predetermined length in each direction, a unit for measuring radii of the pattern in the radial directions from the origin in response to the picked-up binary converted data, a unit for determining a center line of the pattern in the picked-up binary converted data array by the measured length of the first directions, and a unit for encoding the measured length of the second directions to numerals each corresponding to one length of each of the second directions. The reference circuit receives the coded numerals for a reference pattern and forms a coded reference in response to the coded numerals. The determination circuit receives coded numerals for a inspection pattern, compares a code in response to the received coded numerals with the coded reference in the reference circuit, and determines a fault in the inspection pattern.

22 Claims, 23 Drawing Sheets

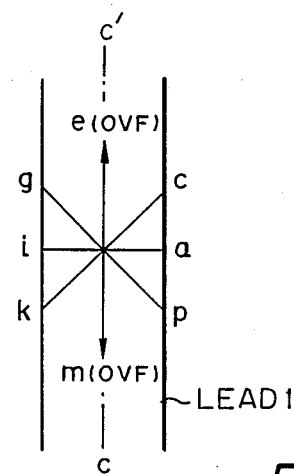
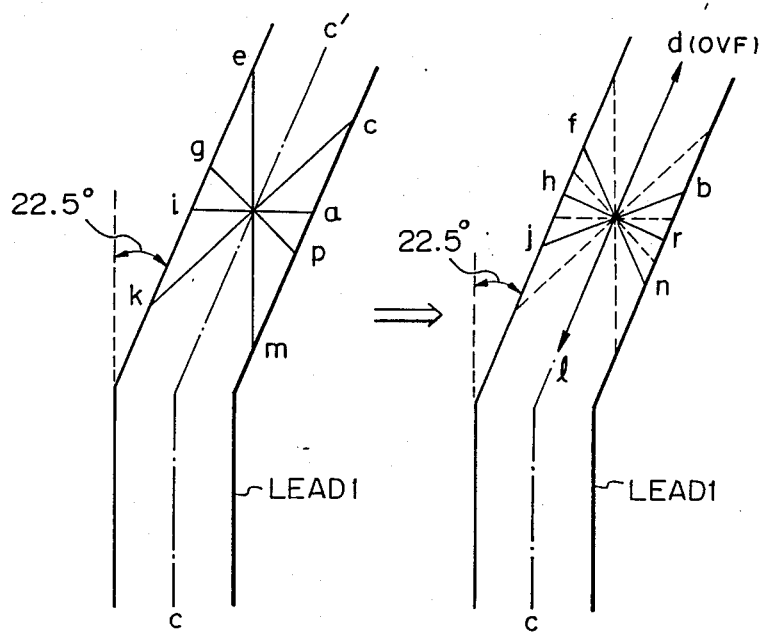
Fig. 22a
Fig. 22b
Fig. 22c

DATA ARRAY

PATTERN INSPECTION SYSTEM

BACKGROUND OF THE INVENTION

1. Field of the Invention

The present invention relates to a pattern inspection system.

The pattern inspection system can be used to inspect patterns of leads on a printed circuit board (PCB), and patterns of a semiconductor chip, etc.

2. Description of the Related Arts

Recently, an improvement in the inspection of patterns on a PCB has been urgently sought, to improve the reliability of system products provided with such PCBs.

Such inspections were carried out by visual observation with a microscope, but the use of extremely complex and miniaturized patterns, and the requirements for reductions in labor and production costs, has led to attempts to develop an automatic inspection system therefor.

JPP No. 58-207633 discloses a system for automatically inspecting patterns on a PCB. In this system, the patterns are optically scanned and, converted into electrical signals. The electrical signals are encoded into binary data, and the binary data is stored in a memory. The binary pattern data is then applied to spatial filters having specific characteristics to extract features of the patterns and detect any abnormalities in the patterns. More specifically, the above spatial filters detect faults by defining shapes which occur in the patterns to be inspected. The binary pattern data is consecutively compared with the spatial filters. If overlapping portions are detected between the input binary pattern data and one of the spatial filters, the system defines those overlapping portions as pattern error portions.

The above spatial filters are designed to act only with a specific pattern and, as a result, the system can not be used to inspect a variety of patterns. Thus, the application of the system is limited. In addition, each spatial filter has a two dimensional shape, and it is difficult to optimize the arrangement of the spatial filter for each pattern. Misjudgments are liable to occur during the inspection.

JPP No. 59-74627 also discloses a method and apparatus for inspecting patterns of photomasks used for PCBs. The apparatus includes an optical means, a scanner, a binary coding means, a memory, an inspection means, and a display. In this apparatus, the inspection means is provided with a picture element type length measurement means having radial directional scales. The length measurement means is applied on a matrix data plane in the memory stored binary coded pattern scan data, to obtain a width of the pattern on the PCB.

The apparatus does not position a center of the width of the pattern. As a result, a correct inspection can not be realized. Also, the apparatus does not use a reference dictionary for comparing actual pattern data. Thus, there is a low inspection accuracy. In addition, the binary coded pattern scan data is not classified by the validity of the width of the pattern. This results in a considerable lengthening of the inspection time and limits the invention to general inspection technology. Furthermore, this apparatus can not detect a two dimensional fault of the pattern, for example, a break of the pattern in a longitudinal direction, and a narrow space between adjacent patterns, etc.

SUMMARY OF THE INVENTION

An object of the present invention is to provide a pattern inspection system by which the patterns on a variety of devices can be inspected.

Another object of the present invention is to provide a pattern inspection system having an improved fault detection accuracy.

Still another object of the present invention is to provide a pattern inspection system which is easily applicable to the inspection of a variety of patterns.

Yet another object of the present invention is to provide a pattern inspection system having a compact circuit configuration and capable of performing a high speed inspection.

According to the present invention, there is provided a system for inspecting patterns on an article, including a unit for optically sensing the pattern and outputting electrical signals in response to the sensed values a unit for converting the electrical signals to binary data of a logical one or zero by a predetermined threshold value a unit for storing the binary converted data in a matrix form corresponding to the sensed pattern and a unit including a gate circuit having main gate circuits for picking-up binary converted data from the store unit in radial directions with respect to an origin and in a plurality of predetermined lengths in the radial directions. A circuit is provided for measuring radii of the pattern in the radial directions from the origin in response to the picked-up binary converted data. This invention further includes a circuit for determining a center line of the pattern in the picked-up binary converted data array by the measured length in first directions and a circuit for coding the measured length of second directions to numerals each corresponding to one length of each of the the second directions, a unit, co-operable with the length measurement unit, for receiving coded numerals for a reference pattern and forming a coded reference in response to the coded numerals and a unit, co-operable with the length measurement unit, for receiving coded numerals for an inspection pattern, comparing a code in response to the received coded numerals with the coded reference in the reference unit, and determining a fault in the inspection pattern.

Preferably, the reference unit may include a memory which sets a bit of an address corresponding to the received coded numerals. Also, the compare and determination unit may read a data of an address corresponding to the coded numerals received thereat from the memory in the reference unit and determine the fault in response to the read data.

The system may further include a unit for correcting the binary converted data array.

The pattern sensing unit may have a resolution for defining a minimum length measured at the length measurement unit.

The radial directions with respect to the origin may include at least eight directions evenly spaced at 45°.

Preferably, the first directions for determining the center line at the length measurement unit may include 16 directions evenly spaced at 22.5°. The second directions at the length measurement unit may include eight directions evenly spaced at 45°.

Preferably, the predetermined lengths in the radial directions for the gate circuit have the same length.

The radius measurement circuit in the length measurement unit may measure the length of the pattern in the directions perpendicular to the direction(s) where the length exceed(s) the predetermined length of the gate circuit.

The coding circuit in the length measurement unit may code the length by a first value smaller than a width of the inspection pattern, a second value greater than the width and suitable for measuring the width and a third value greater than the second value, being approximately equal to the predetermined length of the gate circuit, and suitable for detecting the center line perpendicular to the width direction.

The measurement unit may use inverted binary converted data array. The coding circuit in the length measurement unit may code the length by a fourth value smaller than a distance between adjacent patterns and a fifth value greater than the distance.

Preferably, the above can be combined. That is, the coding circuit may code the length by the first value, the second value and the third value, the measurement unit may use inverted binary converted data arrays, and the coding circuit may also code the length by the fourth value and the fifth value. The reference unit and the determination unit are operable for both coded numerals from the length measurement unit.

In addition, the second directions at the length measurement unit may include 16 directions equal to the first directions. The plurality of predetermined length in the radial directions for the gate circuit have the same length. A first data array set of eight directions even spaced at 45° is used for detecting a width of the pattern, and a second data array set of eight directions evenly spaced at 45° and shifted 22.5° from the above directions is used for detecting the width of the pattern when a reasonable center line is not detected by the first data array set.

Furthermore, the gate circuit may also include a plurality of pairs of sub-gate circuits. Each pair of sub-gate circuits picks up data at both sides opposing and adjacent the main gate circuit picking-up data array of one of eight radial directions and at circumferential ends, and detects the center line of the pattern when the reasonable center line is not detected by the data array of the main gain circuit.

BRIEF DESCRIPTION OF THE DRAWINGS

Other objects and features of the present invention will be described below in detail with reference to the accompanying drawings, in which:

FIGS. 22a to 22e are diagrams of the operation of a second embodiment according to the present invention;

DESCRIPTION OF THE PREFERRED EMBODIMENTS

Figure 1:
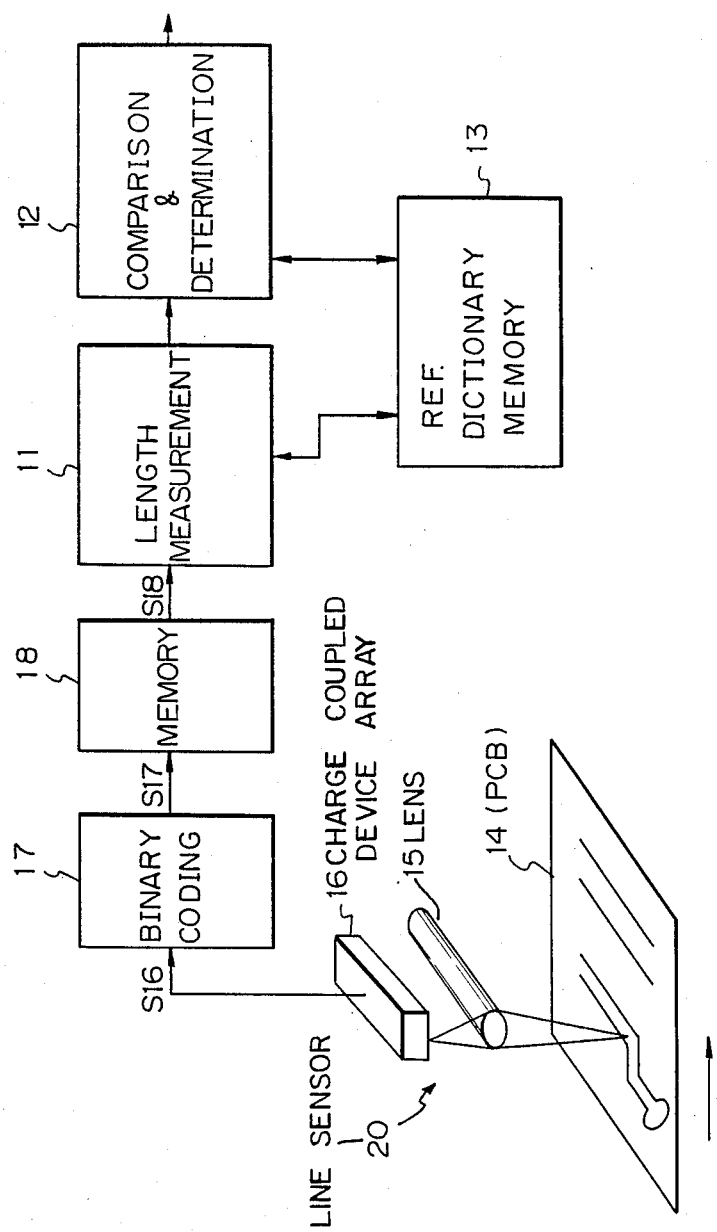
FIG. 1 is a block diagram of an embodiment of a pattern inspection system according to the present invention.

In FIG. 1, a pattern inspection system includes a line sensor 20 including a lens 15 and a charge-coupled device (CCD) array 16, a binary coding circuit 17, a memory 18, a length measurement circuit 11, a comparison and determination circuit 12 and a reference dictionary memory 13.

The pattern inspection system compiles reference dictionaries of flawless patterns prior to inspection and stores the same in the reference dictionary memory 13. It then inspects actual patterns by comparing them with those in the reference dictionary memory 13.

The operation for compiling the reference dictionary will be described with reference to FIG. 2.

Figure 3:
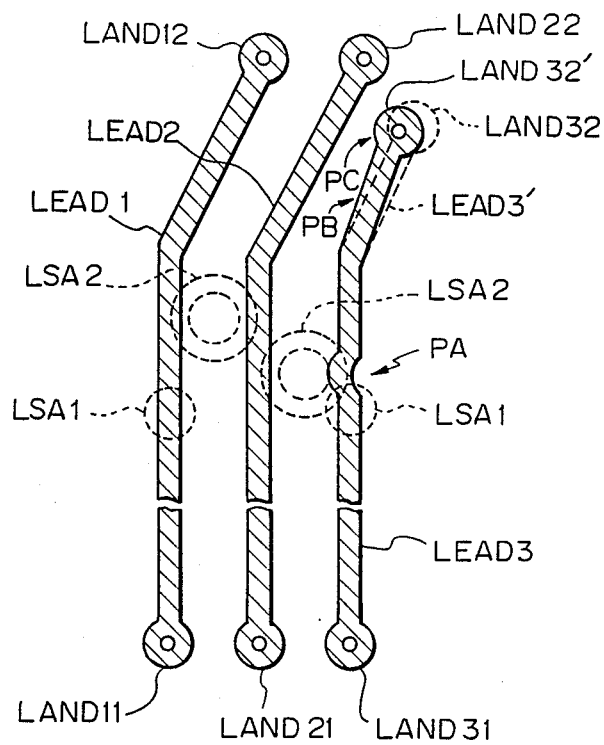
FIG. 3 is a partial enlarged view of patterns on a printed circuit board shown in FIG. 1.

Prior to the operation, a flawless pattern reference PCB 14 is positioned beneath the line sensor 20 incorporating the lens 15 and the CCD 16. FIG. 3 is a partial enlarged view of the PCB 14 in FIG. 1. In FIG. 3, shaded portions show conductive patterns. Each conductive pattern consists of a lead portion, e.g., LEAD1, and a pair of land portions, e.g., LAND11 and LAND12, provided at each end and having apertures for inserting, for example, pins of a semiconductor device. In FIG. 3, a lead portion LEAD3 and a dotted land portion LAND32 shown by a dash line represent flawless patterns, and a shaded lead portion LEAD3' and a shaded land portion LAND32' show flawed patterns. When compiling the reference dictionary, of course, the flawless pattern reference PCB 14 is used.

Steps S001 to S005 in FIG. 2 will now be explained.

In step S001, the line sensor 20 scans patterns on the PCB 14, and the CCD array 16 outputs a plurality of analog electrical signals S16. In step S002, these signals S16 are encoded into binary data S17 by comparison with a threshold value at the binary coding circuit 17.

The binary data is "1" at the portions patterned by reflective material, e.g., the lead portions and the land portions, and "0" at non-patterned portions. Due to this binary coding, the patterned portions and the non-patterned portions can be clearly discriminated. In addition, the binary coding contributes to a reduction of a memory storage area of the memory 18 and an increase in the speed of data handling.

Figure 4A:
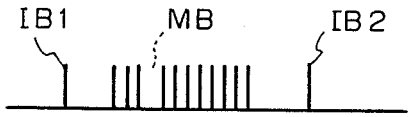
FIGS. 4a and 4b are charts explaining an isolated bit compensation.
Figure 4B:
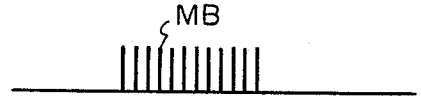

Optionally, in step S003, an isolated bit compensation (correction) can be achieved after the binary coding step. This is a data correction process wherein, when binary coded data is given in a longitudinal direction of the line sensor 20 as shown in FIG. 4a, isolated "1" bits IB1 and IB2, which correspond to non-patterned portions, may be caused by noise and should be "0", and a missing bit MB corresponding to the patterned portion should be "1". The isolated bit compensation eliminates this discontinuity by rejecting the surplus isolated bits IB1 and IB2 and adding an omitted isolated bit MB, as shown in FIG. 4b. Thus increases the reliability of the data processing.

The binary data, optionally subjected to the above compensation procedure, are stored in the memory 18 in step S004.

The above operations are continuously effected for a desired region of the PCB 14, to store the binary data in the memory 18 in a matrix form. The resolution of each binary data is, for example, 5 μm×5 μm, for the PCB pattern inspection.

After the binary data is stored in a matrix form, in step S005, the above isolated bit compensation (correction) process is applied in a traversal direction perpendicular to the longitudinal direction of the line sensor 20.

Figure 5:
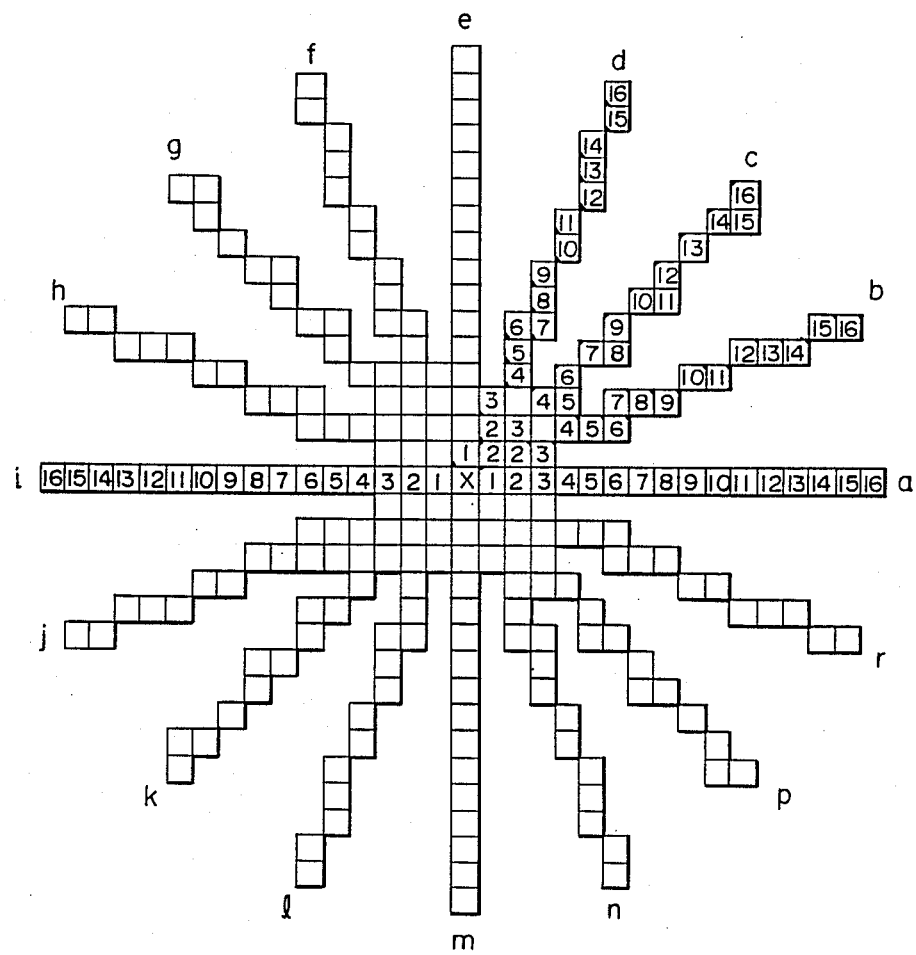
FIG. 5 is a data array in which the length measurement is used.
Figure 6:
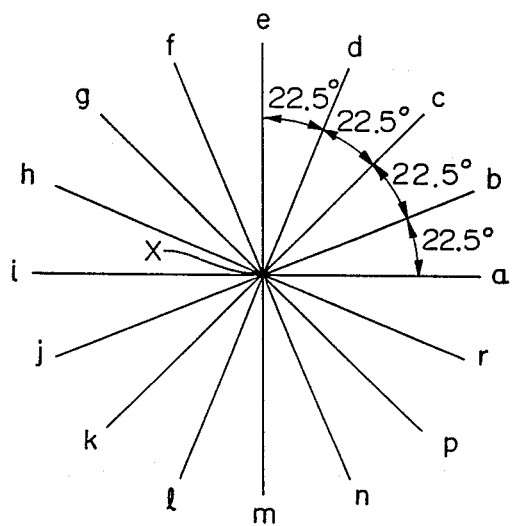
FIG. 6 is a diagram indicating directions of the data array in FIG. 5.

In a step S006 the binary coded pattern data S18 is sent to the length measurement circuit 11, and the radius measurement with respect to an origin X of a lead portion is effected. The length measurement circuit 11 includes a gate circuit having main radial directional gate circuits (not shown) constructed to pick up the binary coded pattern data arranged in a matrix in radial directions, as shown in FIG. 5. The data pick-up is formed in sixteen radial directions with respect to an origin X, i.e., X-a, X-b, X-c, - - - , X-r, as shown in FIGS. 5 and 6. As the data pick-up is effected to the discrete two dimensional matrix data, the data picked-up through the gate circuit is discretely arranged, but the continuity of the data in each direction can be established as shown in FIG. 5. In FIG. 5, numerals 1 to 16 indicate distances from the origin X. Each numeral indicates the same distance. Also, as shown in FIG. 5, the boxes without a mark or boxes marked in the same corner are all in line in the same direction.

A radius (length) of the data pick-up in each direction or a diameter of the data pick-up in opposite directions is defined such that the diameter of the lead portion is greater than the width thereof, as shown by a dotted circle LSA1 (length sensing area) in FIG. 3. The diameter of the lead portion can also be smaller than the distance between adjacent lead portions as shown by the dotted circle LSA2.

Referring to FIG. 5, the radius is 16×5 μm=80 μm, but the diameter is (16×2)×5 μm=160 μm. 5 μm is the width of each scanned area as set forth above.

Figure 7:
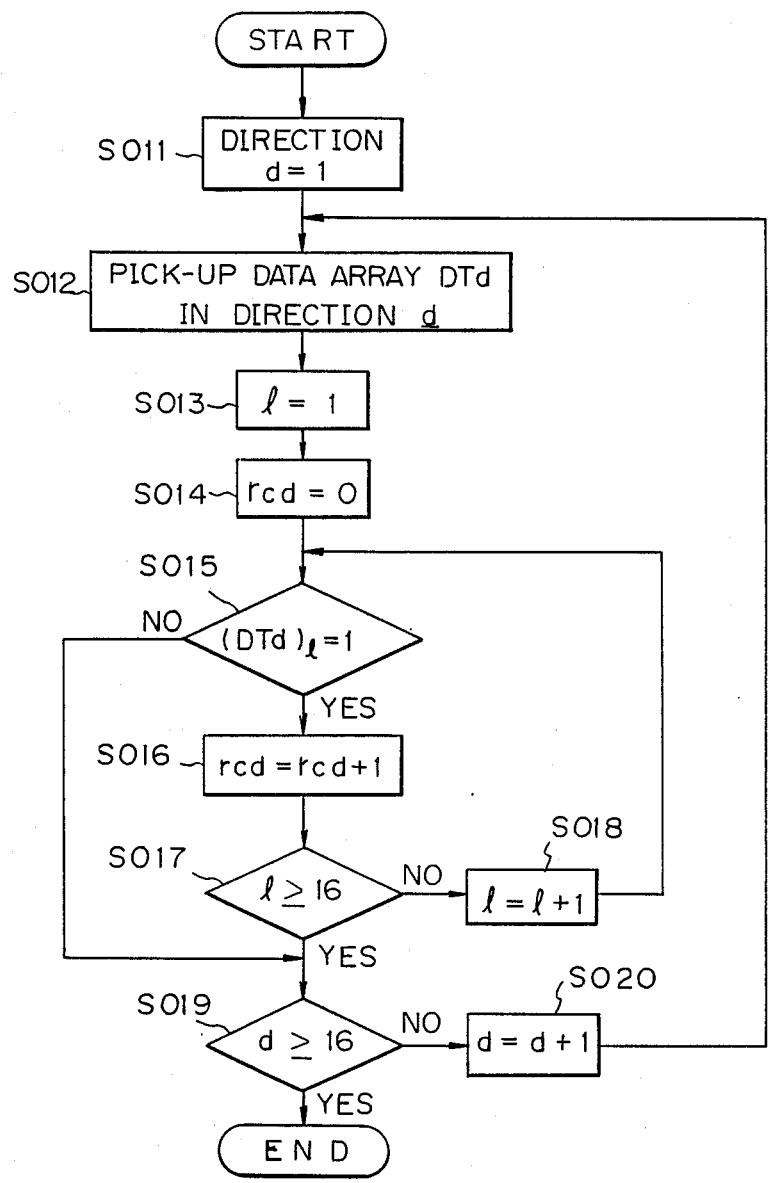
FIG. 7 is a flow chart for performing a radius measurement.

The radius measurement in each direction is carried out by, for example, a microprocessor in the length measurement circuit 11, as shown in FIG. 7.

At step S011, a direction index d is set to "1", where d=1 indicates the direction a in FIGS. 5 and 6. At step S012, the data array DTd is picked-up. At step S013, a radial length index l is set to "1", and at step S014, a radius counter rcd is cleared. When $(DTd)_l = 1$ at step S015, "1" is added to rcd, i.e., rcd=rcd+1 at step S016, and the operations of steps S015 to S018 are repeated until l reaches 16 at step S017. When $(DTd)_l = 0$ at step S015, the above radius count is bypassed and the control is transferred to step S019.

The above operation is repeated at steps S019 and S020 until the direction index d reaches 16, i.e., the direction r in FIGS. 5 and 6.

Actual radii $Ar_1$ to $Ar_{16}$ of the directions a to r are calculated by the following formula:

$$Ar_i = rci \times 5 \; \mu m \qquad (1)$$

where, i=1 to 16

In the following calculation, the counted radii $r_1$ to $r_{16}$ ($\equiv rc_1$ to $rc_{16}$) are used for the convenience of the data processing.

In step 007 (S007), centering is carried out by using the radii $r_1$ to $r_{16}$. This centering operation will be described with reference to FIGS. 8 and 9.

Figure 9:
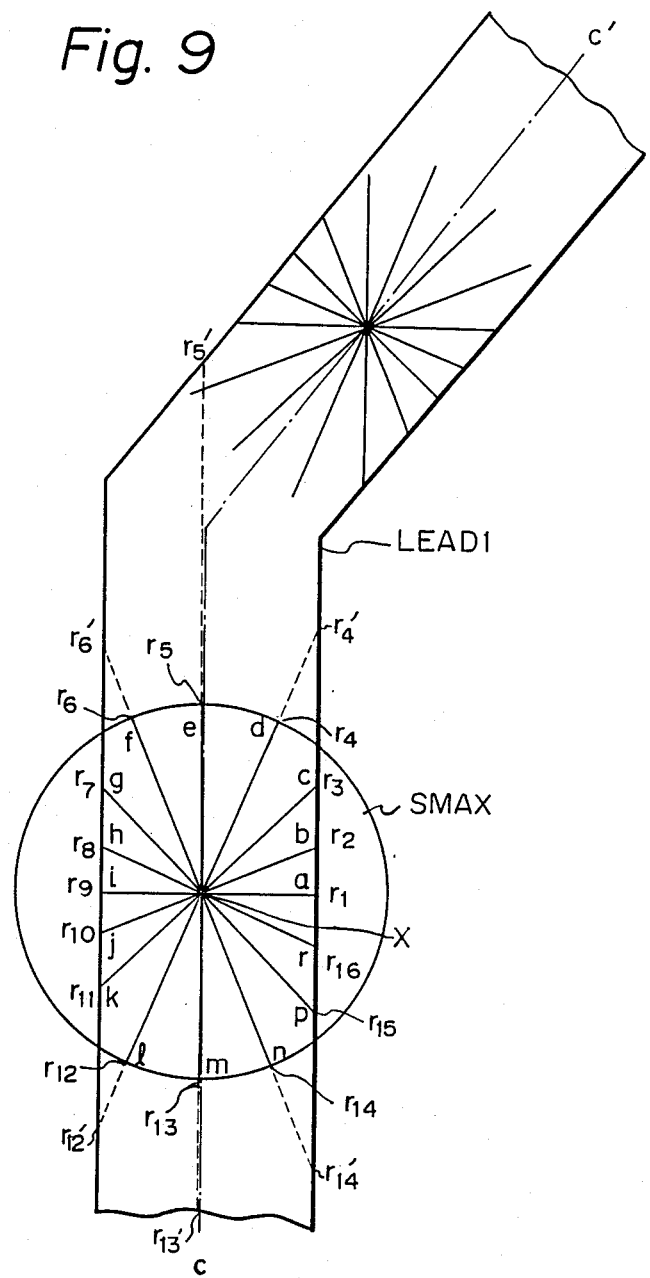
FIG. 9 is a diagram explaining the centering operation.

In FIG. 9 shows the radii $r_1$ to $r_{16}$, wherein a reference SMAX, 16 in this example, denotes a maximum radius for the length measurement. Note that the lengths (radii) at the directions d, e, f, l, m and n should be $r'_4$, $r'_5$, $r'_6$, $r'_{12}$, $r'_{13}$, and $r'_{14}$. However, due to the limitation of the length measurement, the actual lengths thereof are $r_4$, $r_5$, $r_6$, $r_{12}$, $r_{13}$ and $r_{14}$. This should be considered for the centering.

Figure 8:
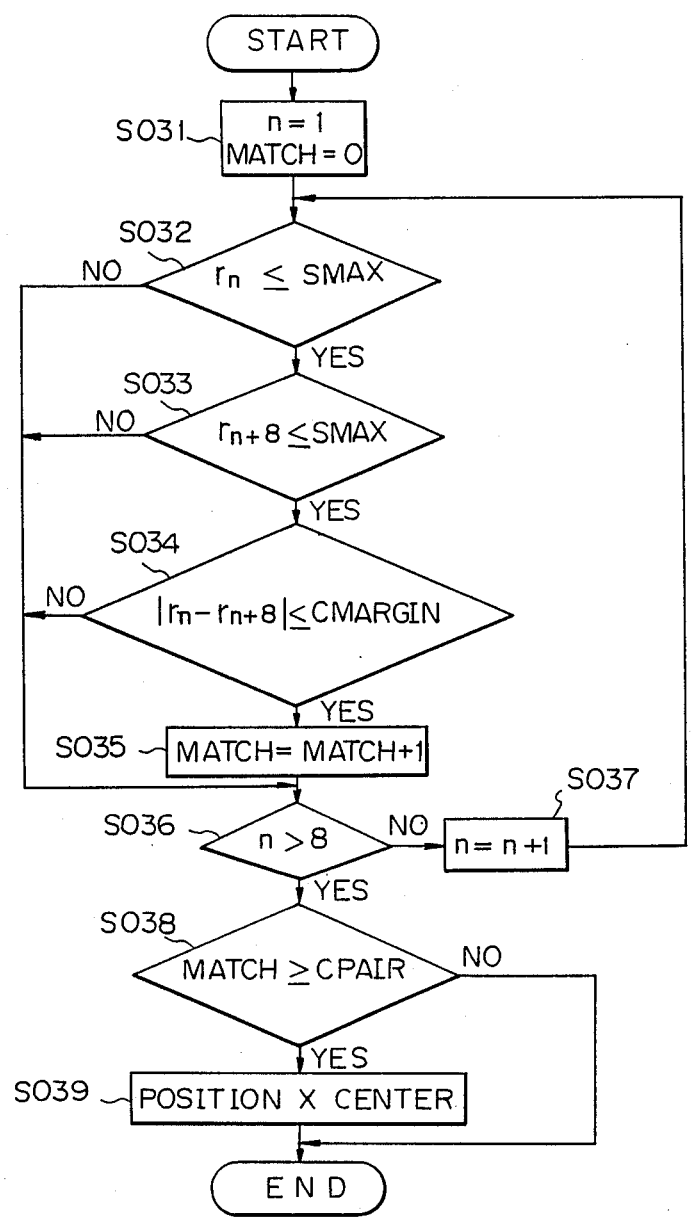
FIG. 8 is a flow chart for performing a centering operation.

In FIG. 8, an initialization is carried out at step S031. Here, n denotes the direction index and MATCH denotes a counter for matching a pair of opposed radii with respect to the origin X in FIG. 5.

At steps S032 and S033, a validity check of the measured length for opposing directions, for example, the directions a and i, is performed. If the following conditions are satisfied, both opposing radii are considered satisfactory.

$$r_n \leq SMAX \qquad (2)$$

$$r_{n+8} \leq SMAX \qquad (3)$$

If these criteria are not satisfied, a pair of radii, such as $r_4:r_{12}$, $r_5:r_{13}$ and are considered false, can not be used for the centering operation. When the above conditions are satisfied, a difference between valid opposing radii: $|r_n - r_{n+8}|$ is compared with a margin CMARGIN at step S034. If $$|r_n - r_{n+8}| \leq CMARGIN \qquad (4)$$

the origin X of the directions n and n+8 is deemed to be a center of the lead portion LEAD1 at a point in the directions n and n+8. Then, at step S034, the match counter MATCH is increased by one (S035). The above operation of steps 032 to 034 is repeated until n is greater than 8 (steps S036 and S037).

After completion of the matching determination for all directions, if the match counter MATCH is equal to or greater than a predetermined value CPAIR, e.g. 2, (at step S038), the origin X is determined to be the true center position at the point in the opposite directions at step S039.

In FIG. 9, the match counter MATCH may be five, because differences between opposing radii are smaller than CMARGIN at the directions a:i, b:j, c:k, g:p and h:r.

By consecutively performing the above centering for a point of the origin, a center line C—C' is defined as shown in FIG. 9.

In step S008, the diameter calculation and coding of the diameter is performed. First, calculation of the diameter is carried out by the following formula:

$$l_{2n-1} = r_{2n-1} + r_{2n+7} - 1 \qquad (5)$$

$n: 1 \sim 4$ $l_{2n-1}$ : diameter in the directions $(2n - 1)$ and $(2n + 7)$

If $n-1$, $l_1 = r_1 + r_9 - 1$. That is, the diameter $l_1$ is a diameter in the directions a and i in FIG. 5. The subtraction of one $(-1)$ means a rejection of the origin X.

Figure 10:
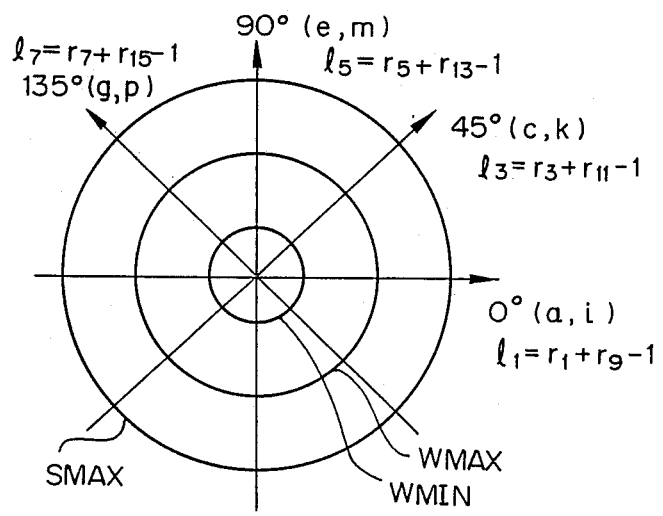
FIG. 10 is a diagram of zones used in coding for a lead pattern.

Note that the calculation of the diameter is carried out in the directions a:i, c:k, e:m and g:p, as shown in FIG. 10. As described above, the centering uses the radii in all 16 directions, i.e., at every 22.5° with respect to the origin X, to ensure an accurate positioning of the center.

Second, if the opposing radii satisfy the formula (4), the radii are defined as "PAIRED" or "NOT-PAIRED".

Third, the coding of the diameter is carried out by classifying the diameter into circular zones, as shown in FIG. 10.

For example, WMIN has a length of approximately a half of a width of the pattern, WMAX has a length of approximately twice of the width of the pattern, and SMAX has a length of approximately three times to four times of the width of the pattern.

Figure 11:
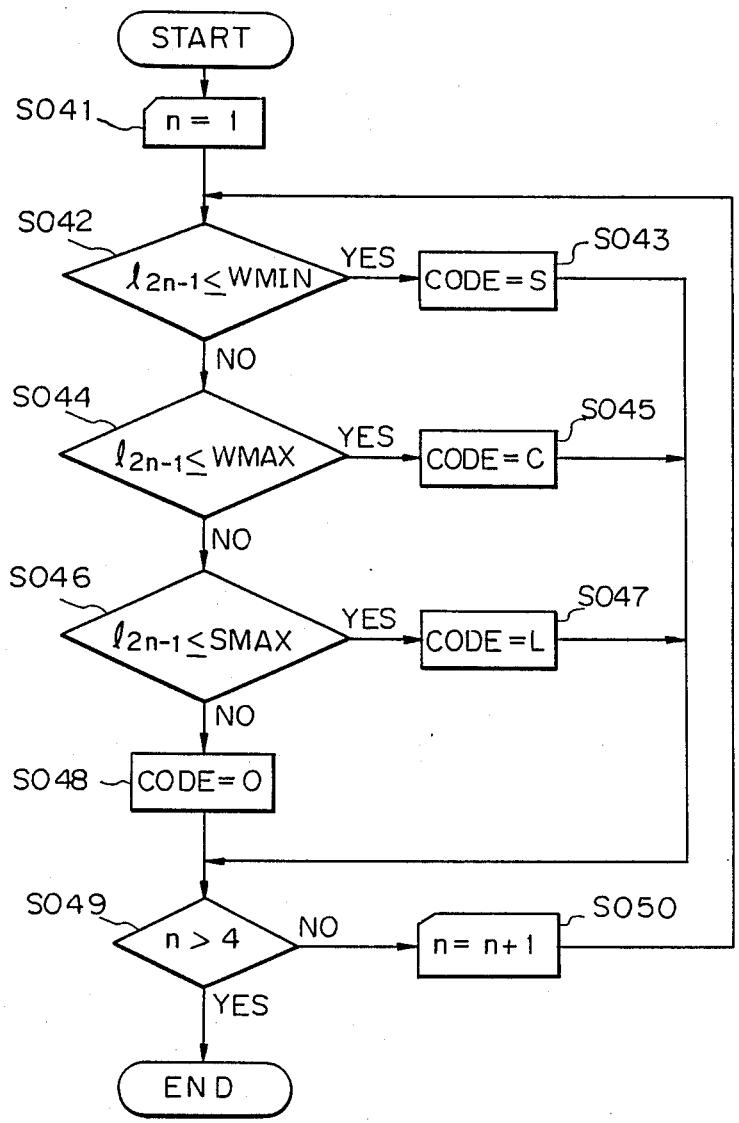
FIG. 11 is a flow chart for performing zone classification.

FIG. 11 is a flow chart for the coding of the diameters. In FIG. 11, reference numerals S, C, L, O indicate "short", "correct", "long" and "overflow".

The above coding is classified into the paired condition and the not-paired condition, as shown in Table 1.

TABLE 1

|  | PAIRED | NOT-PAIRED |
|---|---|---|
| $0 \leq 1 < $ WMIN | S | NS |
| WMIN $\leq 1 \leq$ WMAX | C | NC |
| WMAX $< 1 \leq$ SMAX | L | NL |
| SMAX $< 1$ (overflow) | O | NO |

In Table 1, reference S designates "short" under the PAIRED condition, and reference NS also designates "short" under the NOT-PAIRED condition. An asterisk (*) indicates that one side radius is in an overflow condition.

The above codes are actually expressed by the following numbers.

TABLE 2

| NO | 0 |
|---|---|
| NL | 1 |
| NC | 2 |
| NS | 3 |
| O | 4 |
| L | 5 |
| C | 6 |
| S | 7 |

Each code is expressed by three bits. Accordingly, the codes in four directions a:i, c:k, e:m and g:p are expressed by $3 \times 4 = 12$ bits.

Figure 12:
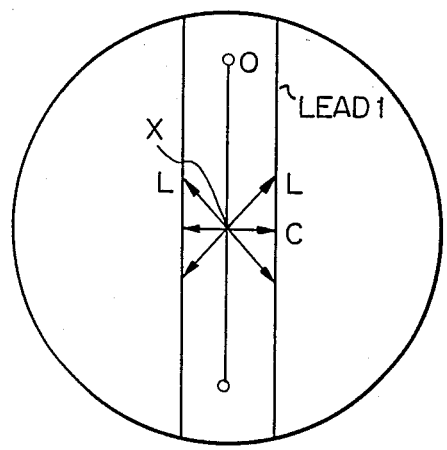
FIGS. 12 and 13 are diagrams of a coding process and a compiling of a reference dictionary.

If the codes C, L, O and L are obtained as shown in FIG. 12, the numerical code becomes "6545".

Figure 13:
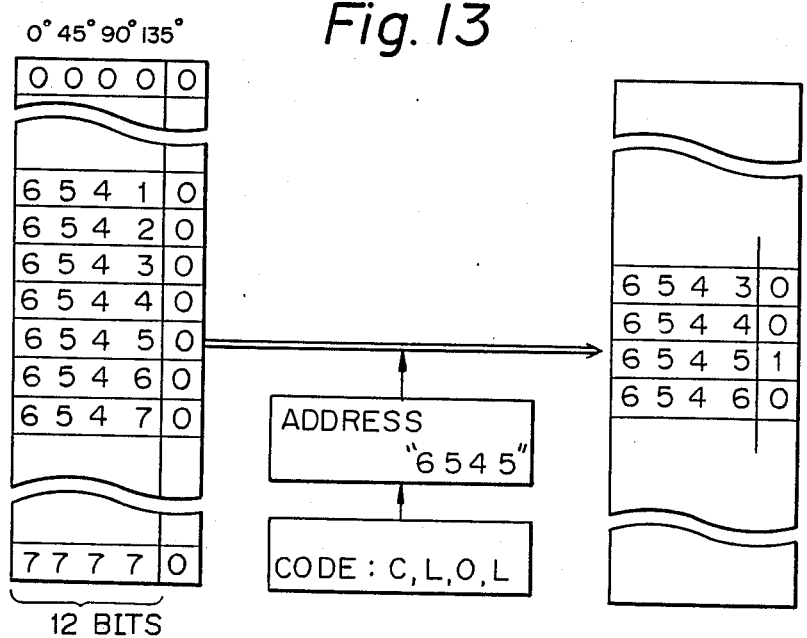

In step S009, the numerical code is used as an address and "1" is set at the address "6545" in the reference dictionary memory 13, as shown in FIG. 13.

Similarly, each combination of the direction and the measured length for the flawless pattern is defined as a reference dictionary in the reference dictionary memory 13.

The coding enables a considerable reduction of a capacity of memory, and simplifies the inspection process.

In addition, general data processing in which the actual value is not used can be performed. This enables the inspection of a variety of patterns.

Figure 14:
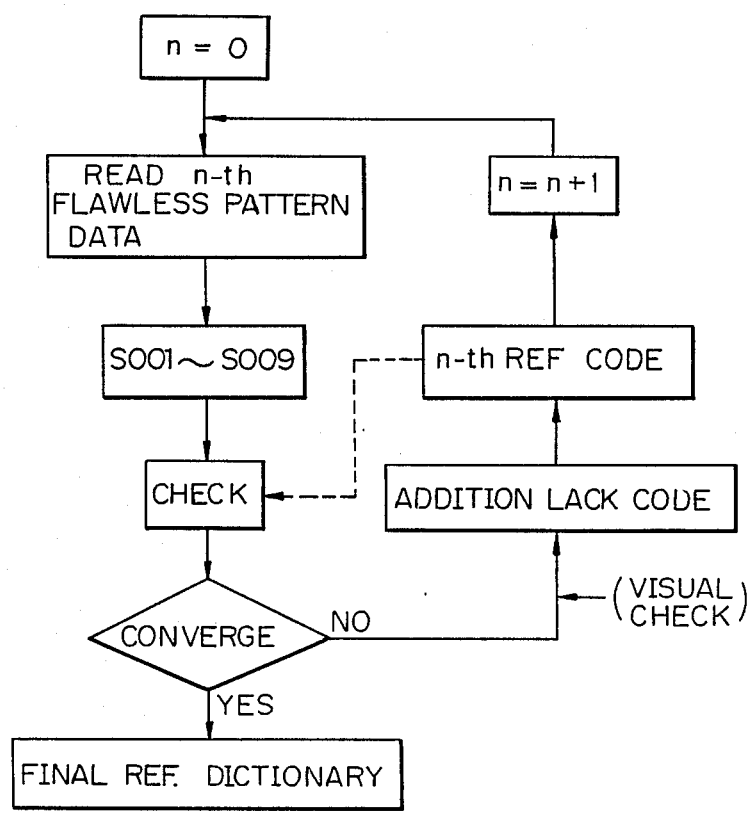
FIG. 14 is a block chart explaining the operation of compiling a satisfactory dictionary.

The above operation is repeated for a plurality of flawless patterns to compile a perfect reference dictionary, as shown in FIG. 14. A visual check can be made by using a display.

If a new pattern inspection is required, a reference dictionary for a new flawless pattern can be compiled.

After the coded reference dictionary is compiled, the inspection of actual patterns is continued with reference to the coded reference dictionary. The pattern inspection system in FIG. 1 is also used for the inspection.

Note, prior to the inspection, an actual PCB to be inspected must be positioned beneath the line sensor 20.

The inspection for a lead portion will be described with reference to FIGS. 15 to 17.

Figure 2:
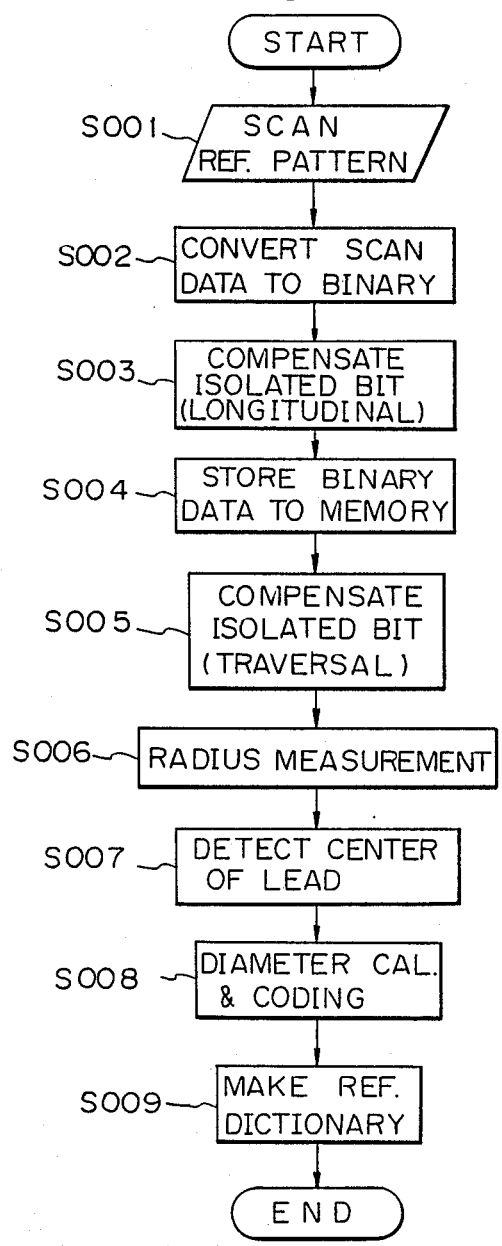
FIG. 2 is a flow chart explaining the make-up of a reference dictionary.
Figure 15:
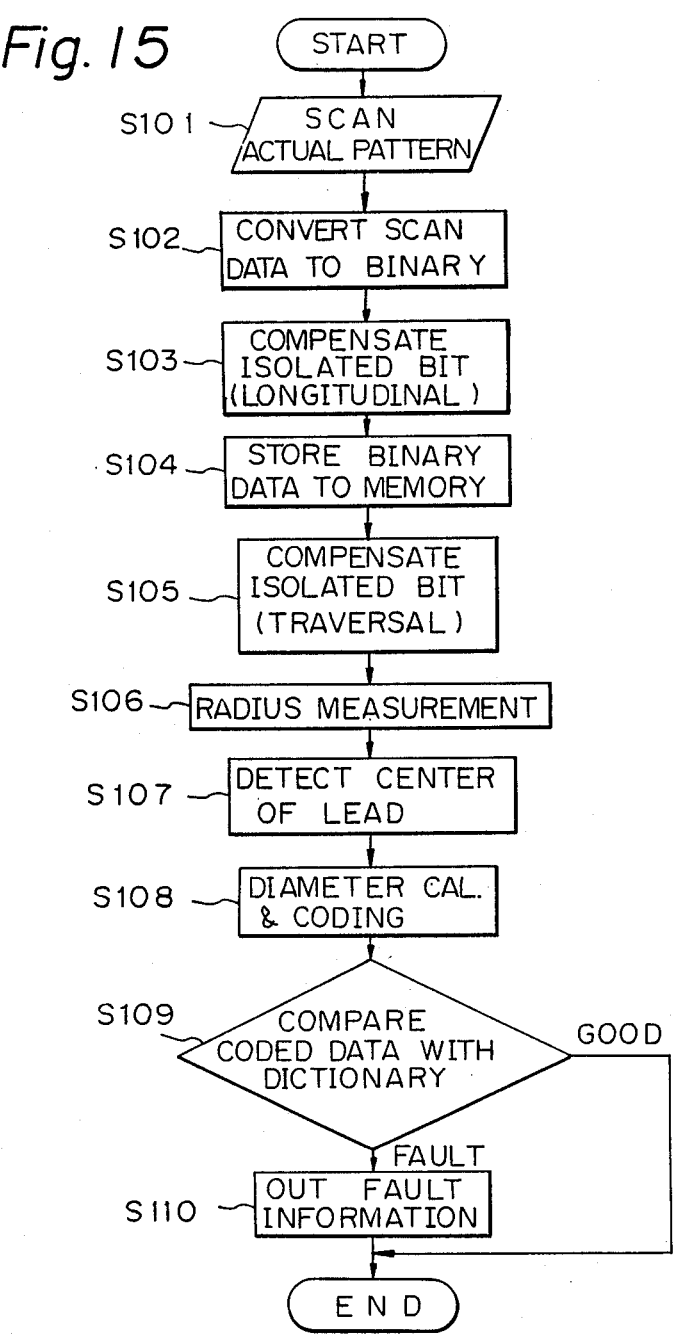
FIG. 15 is a flow chart for performing the inspection of an actual lead pattern.

In FIG. 15, the operations from step S101 to step S108 are similar to the operations from step S001 to step S008 in FIG. 2, as described above. As a result, coded diameters in directions a:i, c:k, e:m and g:p are obtained together with the conditions of either "PAIRED" or "NOT-PAIRED", as shown in Tables 1 and 2.

Figure 16:
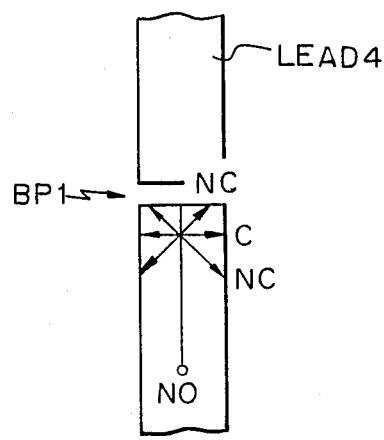
FIG. 16 is a diagram of a break in a pattern.

Assuming that a lead portion LEAD4 having a break at a portion BP1 in FIG. 16 is scanned, and the coded diameters are "C", "NC", "NO", and "NC". According to the translation shown in Table 2, the above coded diameters correspond to an address "6202".

Figure 17:
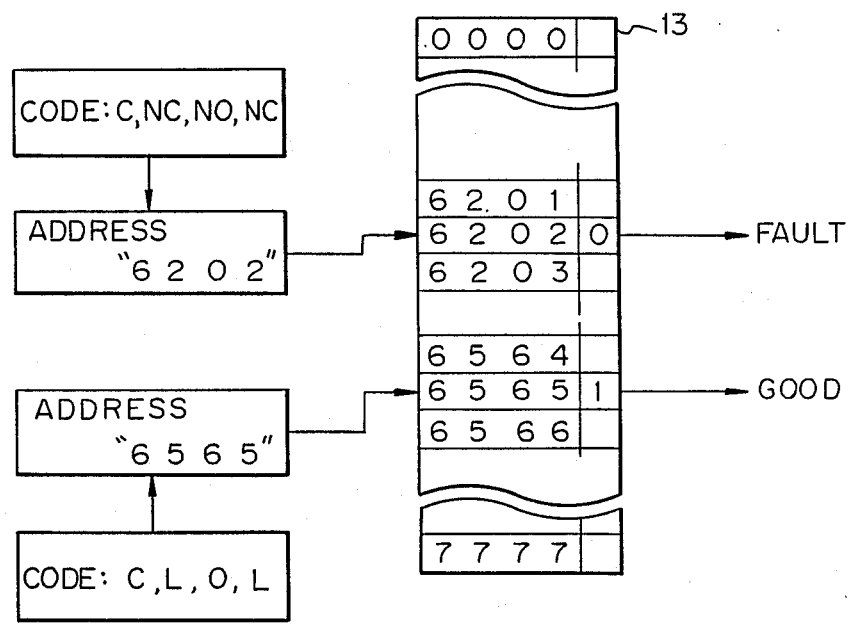
FIG. 17 is a chart for determining whether a pattern is good or faulty.

Referring again to FIG. 15, at step S109, the comparison and determination circuit 12 reads data of the address "6202" from the reference dictionary memory 13 (FIG. 17). Since a defective pattern as shown in FIG. 16 cannot be found in the flawless reference patterns, the data read is "0". Then, the comparison and determination circuit 12 determines the scanned pattern as "FAULT", and outputs fault information at step S110. The fault information may include a position of the faulty pattern.

On the other hand, when the flawless lead portion LEAD1 as shown in FIG. 9 is scanned, the codes may be "C", "L", "O", "L". These codes correspond to an address "6545". The comparison and determination circuit 12 reads data "1" at the address "6545" from the reference dictionary memory 13 and determines the scanned pattern as "GOOD" (FIG. 17).

A variety of pattern defects, such as a bent pattern as shown at a portion PA on a lead portion LEAD3 in FIG. 3, etc., also can be easily detected, in addition to the broken pattern in FIG. 16.

The use of the directional measurement, the coding technology, etc., enables the inspection to be effected easily, at a high speed and with a smaller memory capacity and accuracy.

The pattern inspection system in FIG. 1 can be applied for the inspection of not only the lead pattern as described above but also a space (a mutual pattern) between lead portions, such as a pattern between the lead portions LEAD1 and LEAD2 or LEAD2 and LEAD3 in FIG. 3. The inspection of the space (mutual pattern) will be described as follows.

Figure 18:
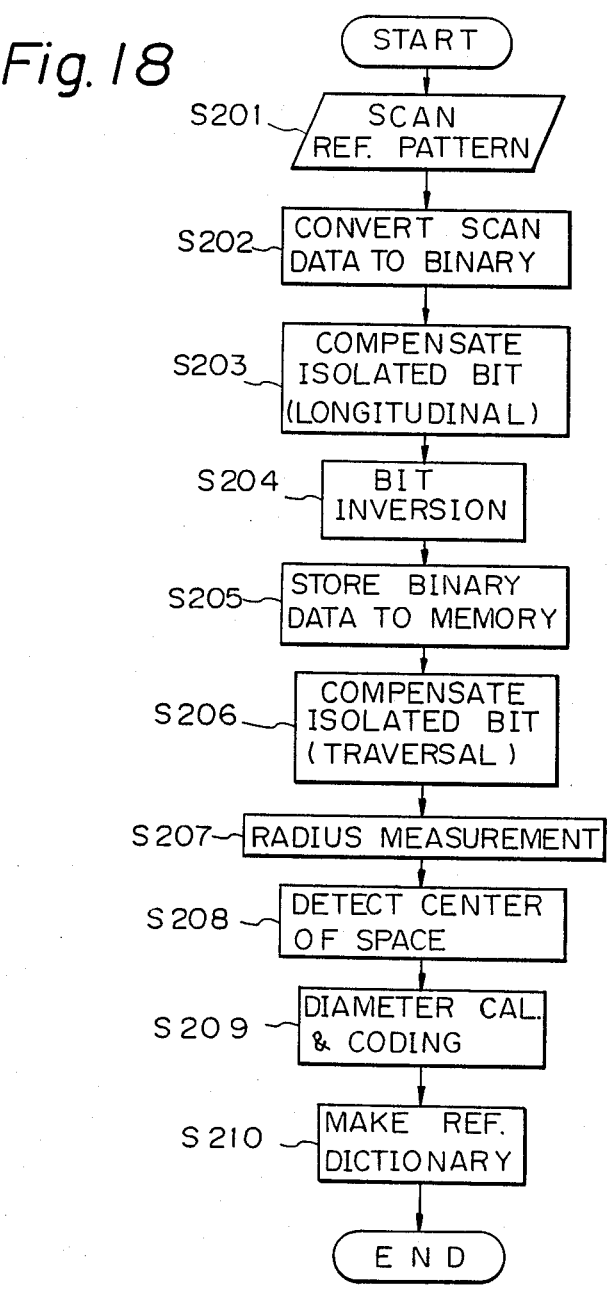
FIG. 18 is a flow chart of a compilation of a reference dictionary for a mutual pattern.

FIG. 18 is a flow chart of the compilation of a reference dictionary for the space. In FIG. 18, the operations of steps S201 to S203 are identical to those of steps S001 to S003 in FIG. 2. At step S204, since the data of the space is "0", a bit inversion is effected to produce the space. The operation of steps S205 to S210 are also similar to those of steps S004 to S009 in FIG. 2. However, there are some differences in the above lead portion reference dictionary.

Figure 19:
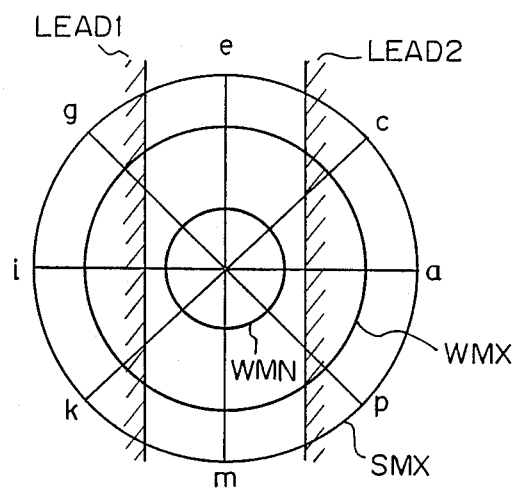
FIG. 19 is a diagram of zones using the coding for a mutual pattern, corresponding to FIG. 10.

First, a dotted circle LSA2 (length sensing area) differs from the LSA1 for inspecting the lead portion shown in FIG. 10. An enlarged LSA2 is shown in FIG. 19. The LSA2 includes an inner circle having a radius WMN, a middle circle having a radius WMX, and an outer circle having another radius SMX. To detect a center of the space between LEAD1 and LEAD2, the radius WMX should be greater than a distance between LEAD1 and LEAD2, but the radius WMN should be smaller than that distance. WMN and SMX can correspond to WMIN and SMAX in FIG. 10. Accordingly, the classification and coding is substantially the same as that in FIG. 2.

WMN is a length of approximately 70% to 80% of a distance of the space, WMX is a length of approximately 1.4 to 1.5 of the distance of the space, and SMX is a length of three to four times of the distance of the space.

Figure 20:
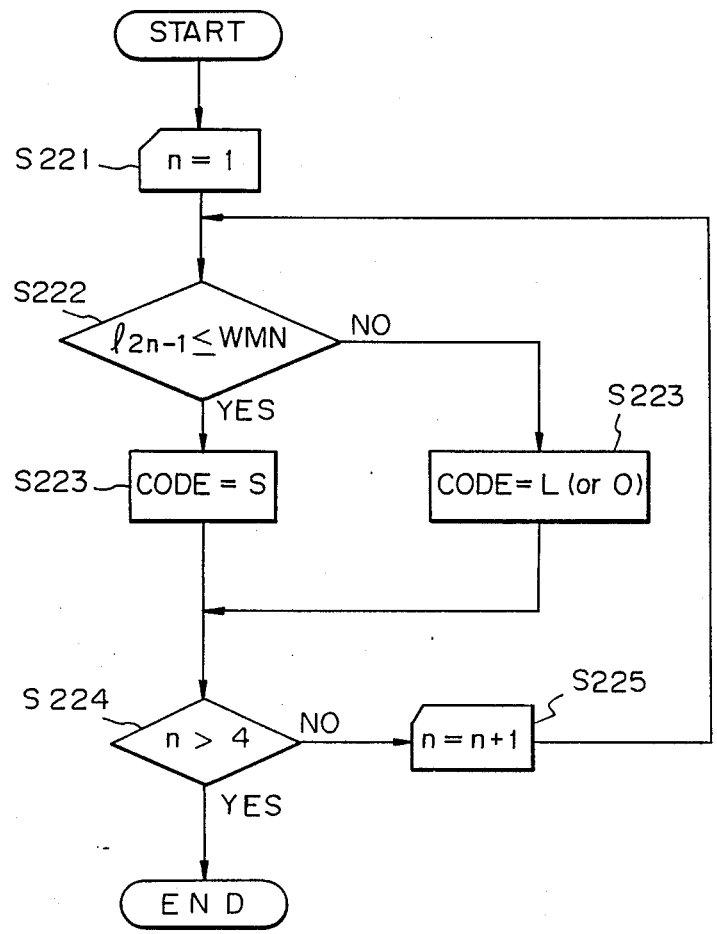
FIG. 20 is a flow chart for zone classifying a mutual pattern, corresponding to FIG. 11.

Second, a flawless space has lengths longer than WMN in all directions a:i, c:k, e:m and g:p, and thus, the coding is very simple as shown in FIG. 20, compared to that shown in FIG. 11. If the diameter $l_{2n-1}$ is longer than WMN, the code is "L (long)", if not, it is "S (short)". The codes of a flawless space are "L", "L", "L" and "L"0 and are transferred to an address "5555", and data at the address "5555" in the reference dictionary memory 13 is set to "1". If the diameter $l_{2n-1}$ is longer than WMX, another code "O (overflow)" can be used instead of "L". Then, data at an address "4444" is set.

After compiling the reference dictionary for the space, the inspection of an actual space is continued.

Figure 21:
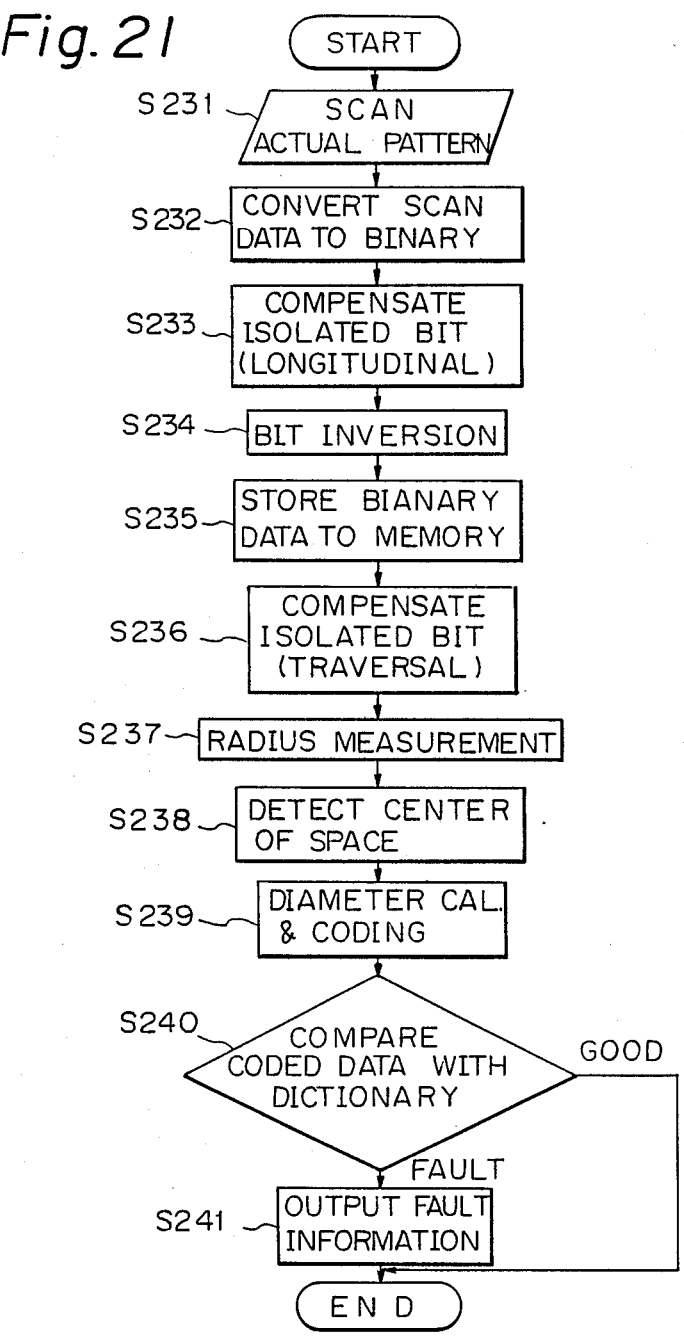
FIG. 21 is a flow chart for inspecting an actual mutual pattern.

FIG. 21 is a flow chart for the inspection of the actual space. Except for an addition of the operation of step S234 based on the same concept as the operation of step S204 in FIG. 18, the other operations of steps S231 and S232, and S235 to S241 are similar to the operations in FIG. 15, except for coding as described above with reference to FIGS. 19 and 20.

If a diameter smaller than WMN in FIG. 19 is detected, a pattern thereat is faulty. Thus defective patterns, as indicated by PA and PB in FIG. 3, can be easily detected.

Preferably, the above lead pattern inspection and the above space inspection should be carried out simultaneously. To compile the reference dictionary, the scanning (step S001 in FIG. 2, step S201 in FIG. 18), the conversion to binary data (steps S002 and S202) and the isolated bit compensation (steps S003 and S203) are common operations. Based on a scanned portion, the compilation of the reference dictionary for the lead pattern, or the compilation of the reference dictionary for the space is carried out.

To inspect the actual patterns, the inspection of the lead pattern or the space is also based on a scanned portion.

If the logic of the conversion at steps S202 and S232 in FIGS. 18 and 21 is reversed, the bit inversion of steps S204 and S234 is omitted.

Another embodiment of the present invention will now be described.

In the above embodiment, 8 directional data arrays evenly spaced at 22.5° are used for the centering, but four-directional data arrays evenly spaced at 45° are preferably used to simplify the data handling. This may result in a lower accuracy of fault detection, particularly of an inclined pattern, and this embodiment is intended to maintain the accuracy even if the pattern is inclined.

FIGS. 22a to 22e are views of enlarged lead patterns to be inspected.

In FIG. 22a, the data array is at 45° and picked-up by the gate circuit in the length measurement circuit 11 in the directions e:m which shows an overflow because of the limitations of the length measurement. Then, the data array spaced at 45° in the direction a:i perpendicular to the direction e:m uses the measurement of the width of the lead portion LEAD1. However, as shown in FIG. 22b, where a portion of the lead LEAD1 has a small width and is inclined at approximately 22.5°, an overflow may not be detected in all directions. Subsequently, by using only the data arrays spaced at 45°, a correct lead portion may not be detected.

Figure 23:
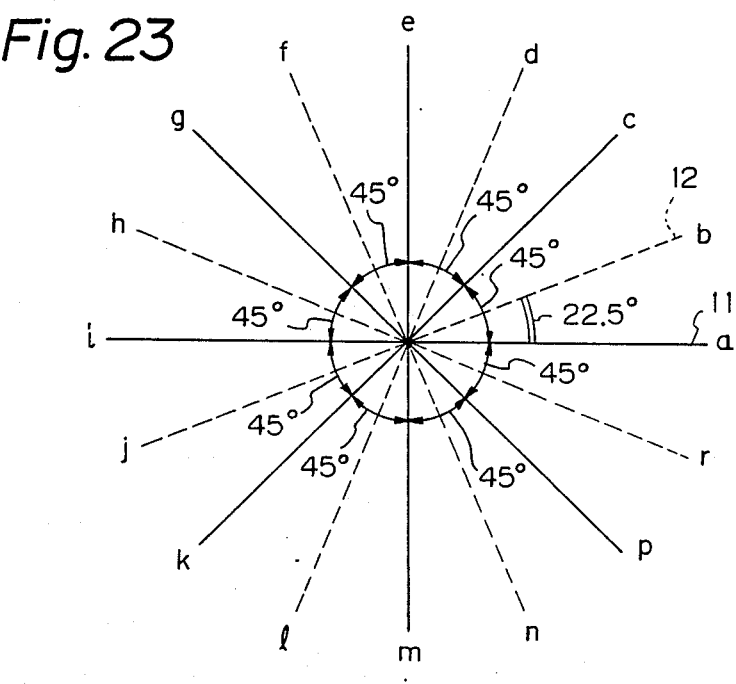
FIG. 23 is a diagram of data arrays in the second embodiment shown in FIGS. 22a to 22e.

In the embodiment, as shown in FIG. 23, a 22.5° system data array 12 shown by dashed lines may be used for the pattern inspection, in addition to a 45° system data array 11 shown by solid lines.

Figure 24:
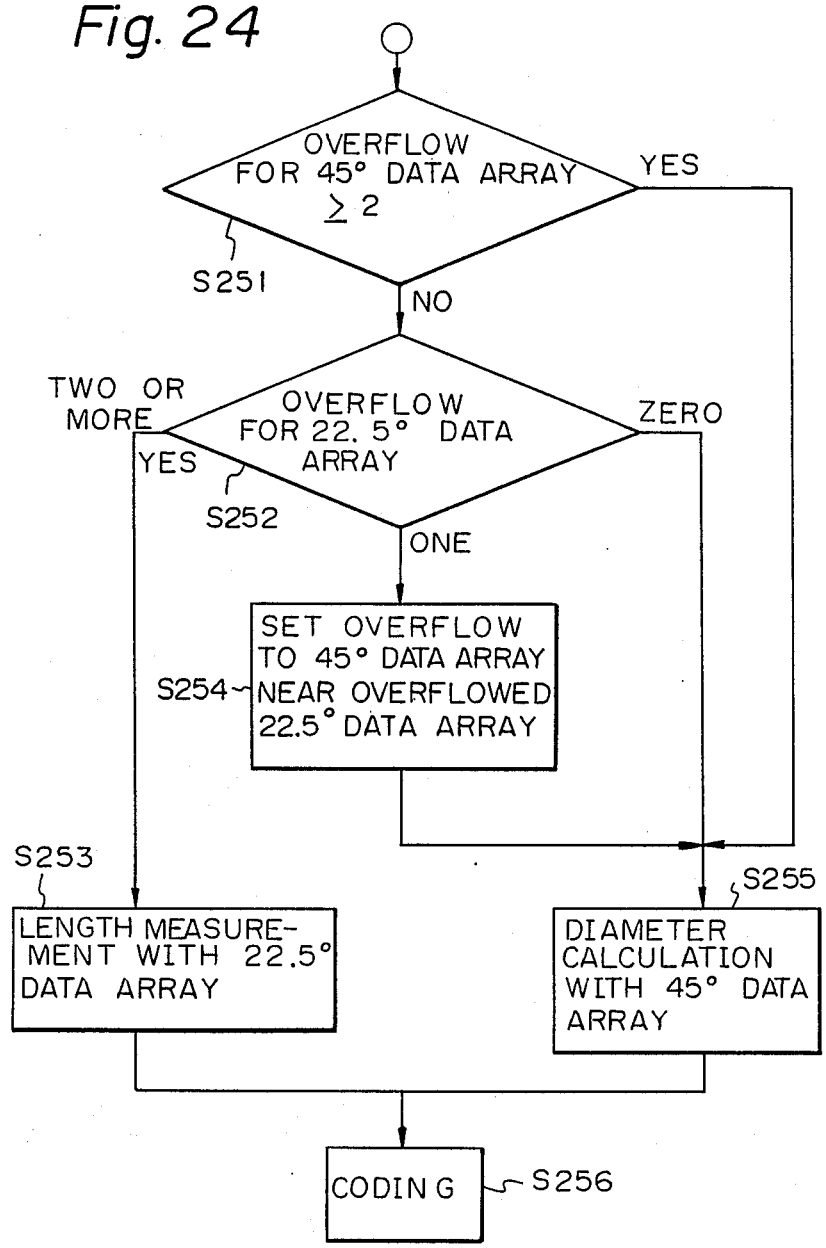
FIG. 24 is a flow chart of the operation of the second embodiment shown in FIGS. 22a to 22e.

FIG. 24 is a flow chart of the length measurement of the embodiment shown in FIG. 23.

Figure 22D:
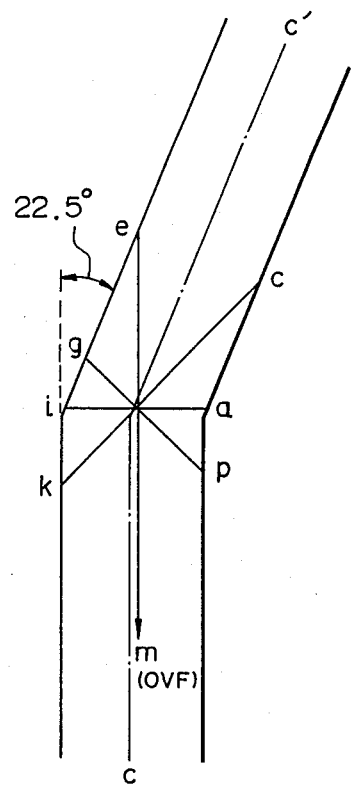
Figure 22E:
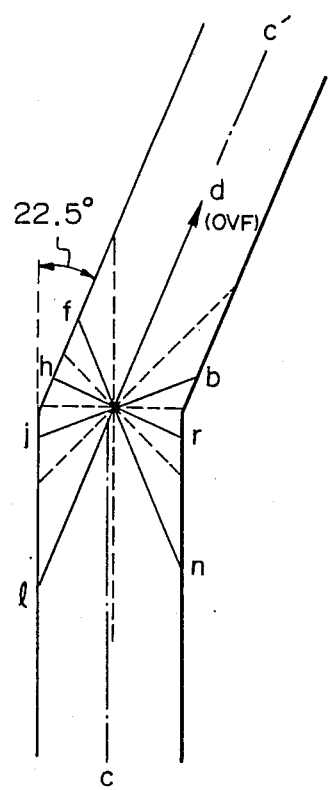

At step S251, the length measurement with respect to a center of the lead portion is effected by using a 45° system data array 11. When two or more overflow directions are detected as shown in FIG. 22, in the directions e and m, the diameter calculation can be effected by using the 45° system data array 11 (step S255). Otherwise as shown in FIG. 22b, the length measurement with respect to the center is carried out by using the 22.5° system data array 12, as shown in FIG. 22c (step S252). When two or more overflow directions are detected as shown in FIG. 22c: the directions d and l, the calculation of the diameter can be carried out by using the 22.5° system data array 11 (step S253). When one overflow is detected by the 45° system data array 11, as shown by the direction m in FIG. 22d, and another overflow is detected by the 22.5° system data array 12, as shown by the direction d in FIG. 22e, the code of the diameter for the 45° data array nearest to the 22.5° data array which has detected the overflow is set to an overflow condition (step S254), and the calculation of the diameter is carried out by the 45° system data array (step S255). If a single overflow is detected by both of the 45° and 22.5° system data arrays, the pattern may be an end or broken pattern. Then the calculation of the diameter is also carried out by using the 45° system data array 11 (step S255). The coding, per se, is identical to that described above (step S256).

The above embodiment can be applied to the inspection of spaces (mutual patterns).

Still another embodiment of the present invention will be described with reference to FIGS. 25 and 26. This embodiment also overcomes the defect of the first embodiment discussed with reference to FIG. 22b.

Figure 25:
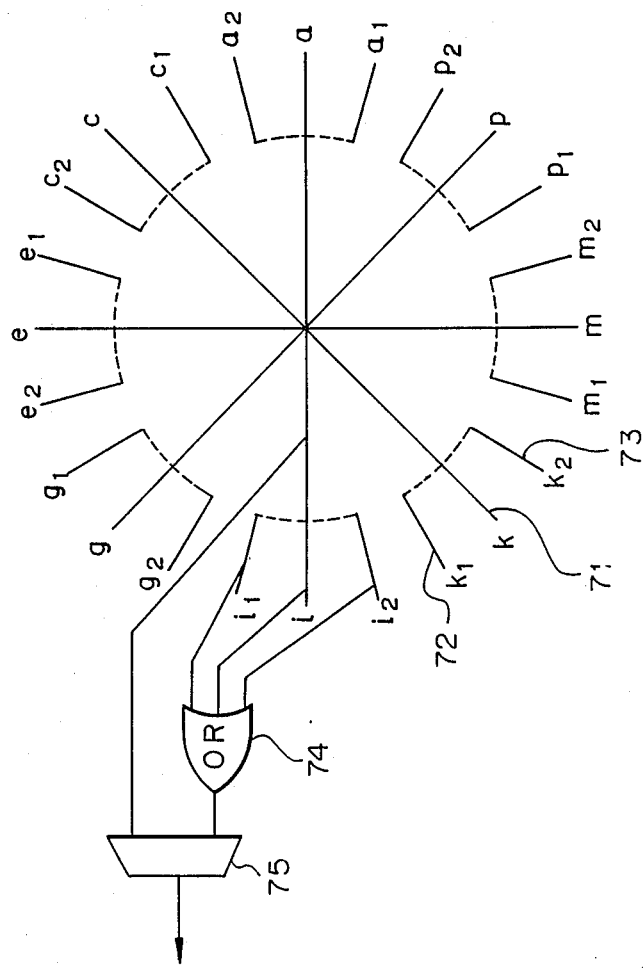
FIG. 25 is a diagram of data arrays of a third embodiment according to the present invention.

In FIG. 25, the length measurement is effected by main data arrays in the directions a, c, e, g, i, k, m and p and pairs of sub data arrays. Each pair being relevant to radial ends and opposed to the main direction at directions a1 and a2 to p1 and p2.

Figure 26:
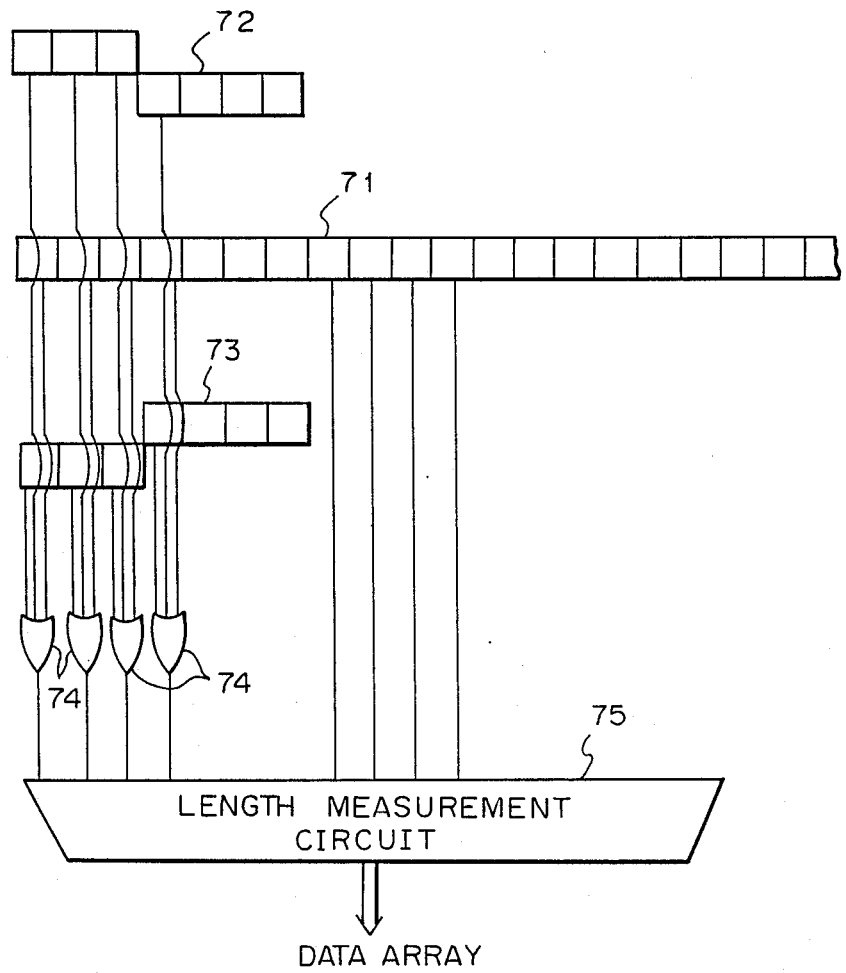
FIG. 26 is a gate circuit of the third embodiment shown in FIG. 25.

An array of gate circuits for the data array in FIG. 25 is shown in FIG. 26. The gate circuit array includes a main gate circuit 71 in the direction i corresponding to a single data array in FIG. 5, a pair of sub gate circuits 72 and 73 in the directions i1 and i2, OR gates 74, and a length measurement circuit 75.

Figure 27A:
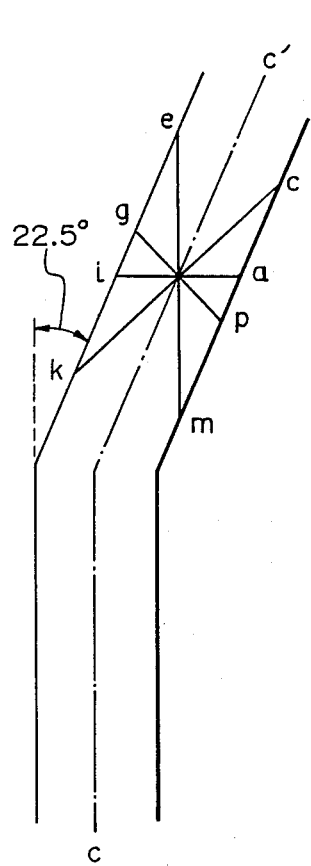
FIGS. 27a and 27b are diagrams explaining the operation of the third embodiment shown in FIG. 25.
Figure 27B:
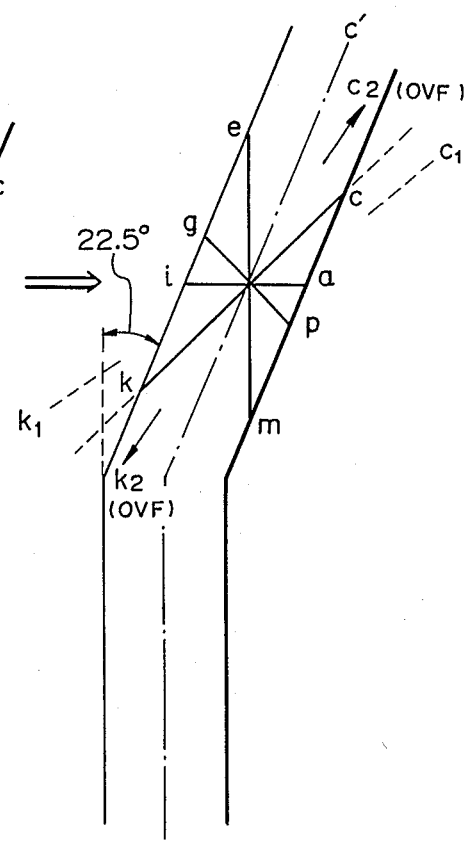

According to the above gate circuit array, a maximum length and an overflow can be detected, as shown in the directions c2 and k2 in FIG. 27b. Note that the overflow is not detected by only the main data array, as shown in FIG. 27a.

The above embodiments can be applied to the inspection of a variety of patterns, for example, the inspection of patterns on a semiconductor chip and a ceramic substrate, etc. When the pattern inspection system is used for the inspection of a pattern of a semiconductor chip, the resolution of the data array should be approximately 0.1 $\mu$m to 0.05 $\mu$m, or less.

A combination of a lens and a photomultiplier, etc., can also be used for the line sensor 20.

The length measurement circuit 11 and/or the comparison and determination circuit 12 can be realized by a hardware circuit or a microprocessor.

Many widely different embodiments of the present invention may be constructed without departing from the spirit and scope of the present invention. It should be understood that the present invention is not limited to the specific embodiments described in this specification, except as defined in the appended claims.

We claim:

1. A system for inspecting patterns on an article, comprising:
    means for optically sensing values of the pattern and outputting electrical signals in response to said sensed values;
    means, operatively connected to said pattern sensing means, for converting said electrical signals to binary data of a logical one or zero, by a predetermined threshold value;
    means, operatively connected to said binary converting means, for storing said binary converted data in a matrix form plane corresponding to said sensed pattern;
    means, operatively connected to said storing means, for determining length measurement of the patterns and including:
    gate means having main gate circuits for picking-up said binary converted data array from said storing means in predetermined radial directions with respect to a point to be inspected in said matrix form plane and in a plurality of predetermined lengths in said radial directions;
    means for measuring lengths of widths both from said point and in first directions defining said widths;
    means for determining a center of said pattern of said picked-up binary converted data array, said center being determined as a point at which both lengths of both widths are approximately equal, and for measuring lengths of widths of said patterns with respect to said center in predetermined second radial directions including said first directions; and
    means for coding said measured lengths in said second directions to numerals each corresponding to one length of each of said second directions;
    means, operatively connected to and co-operable with said length measurement means, for receiving coded numerals of a desired reference pattern of an inspection pattern and forming a coded reference in response to said coded numerals; and
    means, operatively connected to said length measurement means and said reference means, and co-operable with said length measurement means, for receiving coded numerals of the inspection pattern, for comparing a code in response to said received coded numerals with said coded reference in said reference means, and for determining a fault in said inspection pattern.

2. A system according to claim 1, wherein said reference means includes a memory means for setting a bit of an address corresponding to said received coded numerals, and
    wherein said comparison and determination means reads a data of an address corresponding to said coded numerals received thereat from said memory means in said reference means and determines a fault in response to said read data.

3. A system according to claim 2, further comprising means, connected to said binary converting means, for correcting said binary converted data array.

4. A system according to claim 3, wherein said pattern sensing means has a resolution for defining a minimum length measured by said length measurement means.

5. A system according to claim 4, wherein said radial directions with respect to said origin comprise at least eight directions evenly spaced at 45°.

6. A system according to claim 5, wherein said first directions for determining said center line of said length measurement means comprise 16 directions evenly spaced at 22.5°.

7. A system according to claim 6, wherein said second directions of said length measurement means comprise eight directions evenly spaced at 45°.

8. A system according to claim 7, wherein said plurality of predetermined lengths in said radial directions for said gate means have a same length.

9. A system according to claim 8, wherein said radius measurement means in said length measurement means measures a length of said pattern in the directions perpendicular to the direction where the length exceeds said predetermined length of said gate means.

10. A system according to claim 9, wherein said coding means in said length measurement means codes said length by a first value smaller than a width of said inspection pattern, by a second value greater than said width of said inspection pattern for measuring said width, and by a third value greater than said second value, being approximately equal to said predetermined length of said gate means, for detecting a straight line perpendicular to said width of said inspection pattern.

11. A system according to claim 9, wherein said measurement means employs an inverted binary converted data array, and
    wherein said coding means in said length measurement means encodes said length by a fourth value smaller than a distance between adjacent patterns and by a fifth value greater than said distance between adjacent patterns.

12. A system according to claim 9, wherein said coding means in said length measurement means encodes said length by a first value smaller than a width of said inspection pattern, by a second value greater than said width of said inspection pattern for measuring said width, and by a third value greater than said second value, being approximately equal to said predetermined length of said gate means, for detecting a straight line perpendicular to said width direction, wherein said measurement means employs an inverted binary data array, and wherein said coding means in said length measurement means encodes said length by a fourth value smaller than a distance between adjacent patterns and by a fifth value greater than said distance between adjacent patterns, and wherein said reference means and said determination means are operable for said coded lengths from said length measurement means.

13. A system according to claim 6, wherein said second directions of said length measurement means comprise 16 directions equal to said first directions, wherein said plurality of determined lengths in said radial directions for said gate means have a same length, and wherein a first data array set of eight directions evenly spaced at 45° is used for detecting a width of said pattern, and a second data array set of eight directions evenly spaced at 45° and shifted by 22.5° to the eight directions is used for detecting the width of said pattern when a reasonable width is not detected by said first data array set.

14. A system according to claim 13, wherein said radius measurement means in said length measurement means measures a length of said pattern in directions perpendicular to the direction where the length exceeds said predetermined length of said gate means.

15. A system according to claim 14, wherein said coding means in said length measurement means encodes said length by a first value smaller than a width of said inspection pattern, by a second value greater than said width of said inspection pattern for measuring said width, and by a third value greater than said second value, being approximately equal to said predetermined length of said gate means, for detecting a straight line perpendicular to said width direction.

16. A system according to claim 14, wherein said measurement means employs an inverted binary converted data array, and wherein said coding means in said length measurement means encodes said length by a fourth value smaller than a distance between adjacent patterns and by a fifth value greater than the distance between adjacent patterns.

17. A system according to claim 14, wherein said coding means in said length measurement means encodes said length by a first value smaller than a width of said inspection pattern, by a second value greater than said width of said inspection pattern for measuring said width, and by a third value greater than said second value, being approximately equal to said predetermined length of said gate means, for detecting a straight line perpendicular to said width direction.

18. A system according to claim 5, wherein said gate means of said length measurement means further comprises a plurality of pairs of sub-gate means, each pair of sub-gate means picking up data at both sides opposing and adjacent to one of said main gate circuits of one of said eight radial directions and at circumferential ends, for detecting a center line of said pattern when a reasonable center line is not detected by said main gate circuits.

19. A system according to claim 18, wherein said radius measurement means in said length measurement means measures the length of said pattern in the direction perpendicular to the direction where the length exceeds said predetermined length of said gate means.

20. A system according to claim 19, wherein said coding means in said length measurement means encodes said length by a first value smaller than a width of said inspection pattern, by a second value greater than said width of said inspection pattern for measuring said width, and by a third value greater than said second value, being approximately equal to said predetermined length of said gate means, for detecting a straight line perpendicular to said width direction.

21. A system according to claim 19, wherein said measurement means employs an inverted binary converted data array, and wherein said coding means in said length measurement means codes said length by a first value smaller than a distance between adjacent patterns, and by a second value greater than said distance between adjacent patterns.

22. A system according to claim 19, wherein said coding means in said length measurement means encodes said length by a first value smaller than a width of said inspection pattern, by a second value greater than said width of said inspection pattern for measuring said width, and by a third value greater than said second value, being approximately equal to said predetermined length of said gate means, for detecting a straight line perpendicular to said width direction, wherein said measurement means uses an inverted binary converted data array, wherein said coding means in said length measurement means encodes said length by a fourth value smaller than a distance between adjacent patterns and a by fifth value greater than said distance between adjacent patterns, wherein said reference means and said determination means are operable for said coded lengths from said length measurement means, wherein said measurements means uses an inverted binary converted data array, and wherein said coding means in said length measurement means encodes said length by said fourth value smaller than a distance between adjacent patterns and said fifth value greater than said distance between adjacent patterns, and wherein said reference means and said determination means are operable for said coded lengths from said length measurement means.

* * * * *

UNITED STATES PATENT AND TRADEMARK OFFICE
CERTIFICATE OF CORRECTION

PATENT NO. : 4,830,497

DATED : MAY 16, 1989

INVENTOR(S) : SATOSHI IWATA ET AL.

It is certified that error appears in the above-identified patent and that said Letters Patent is hereby corrected as shown below:

FRONT PAGE, [57] ABSTRACT, Col. 1, line 19, "a" should be --an--.

Col. 1, line 24, "and," should be --and--.

Col. 2, line 19, "values" should be --values,--;
line 21, "value" should be --value,--;
line 23, "pattern" should be --pattern,--;
line 36, delete "the" (second occurrence).

Col. 5, line 20, "Thus" should be --This--.

Col. 6, line 5, "$(DTd)_L-1$" should be --$(DTd)_L=1$--;
line 17, equation (1), "rci" should be --$rc_i$--;
line 26, delete "In";
line 49, "and" should be --,--.

Col. 7, line 18, "n-1," should be --n=1--.

Col. 9, line 42, " "L"0 " should be --"L"--.

Col. 14, line 48, "a by" should be --by a--.

Signed and Sealed this

Thirtieth Day of January, 1990

*Attest:*

JEFFREY M. SAMUELS

*Attesting Officer*   *Acting Commissioner of Patents and Trademarks*